United States Patent [19]
Wu et al.

[11] Patent Number: 5,873,901
[45] Date of Patent: Feb. 23, 1999

[54] TREATING RETINAL DAMAGE BY IMPLANTING THIN FILM OPTICAL DETECTORS

[75] Inventors: NaiJuan Wu; Alex Ignatiev, both of Houston, Tex.

[73] Assignee: Space Vacuum Epitaxy Center University of Houston, Houston, Tex.

[21] Appl. No.: 671,408

[22] Filed: Jun. 27, 1996

Related U.S. Application Data

[60] Provisional application No. 60/000,745 Jun. 30, 1995.

[51] Int. Cl.$^6$ ................................. A61N 1/05; A61F 2/14
[52] U.S. Cl. ............................ 607/54; 623/24; 128/898; 607/116
[58] Field of Search .................... 623/4; 607/53, 607/54, 116; 128/898

[56] References Cited

U.S. PATENT DOCUMENTS

| | | | |
|---|---|---|---|
| 4,628,933 | 12/1986 | Michelson | 607/53 |
| 5,016,633 | 5/1991 | Chow . | |
| 5,024,223 | 6/1991 | Chow . | |
| 5,109,844 | 5/1992 | de Juan, Jr. et al. | 607/53 |
| 5,397,350 | 3/1995 | Chow et al. . | |
| 5,556,423 | 9/1996 | Chow et al. . | |

OTHER PUBLICATIONS

H. Lin, N. J. Wu, F. Geiger, K. Xie, and A. Ignatiev, "Photoresponse and fast optical readout for a PbZr$_x$Ti$_{1-x}$O$_3$/YBa$_2$Cu$_3$O$_{7-x}$ thin–film hetersostructure capacitor". *American Institute of Physics*, 6 Mar. 1995, pp. 1172–1174.

Eric King, "Infringement Opinion" of Law Student.

Brindley, G.S. and W.S. Lewin, "The Sensations Produced by Electrical Stimulation of the Visual Cortex," *Journal of Physiology*, 1968, pp. 479–493.

Dobelle, W.H., and M.G. Mladejovsky and J.P. Girvin, "Artificial Vision for the Blind: Electrical Stimulation of Visual Cortex Offers Hope for a Functional Prosthesis," *Science*, vol. 183, Feb. 1974, pp. 440–443.

Dobelle, William H., "Artificial Vision for the Blind—The Summit may be Closer Than you Think," *ASAIO Journal*, 1994, pp. 919–922.

*Primary Examiner*—Jeffrey R. Jastrzab
*Attorney, Agent, or Firm*—Baker & Botts, L.L.P.

[57] ABSTRACT

A method for treating retinal damage by implanting a thin film optical detector based on a dielectric capacitor. When illuminated, the dielectric capacitor generates an electrical field that replaces signals from damaged retinal photoreceptors in the eye. The generated electric field stimulates healthy local nerve endings and are perceived by the patient as light. In a preferred embodiment, the detectors are implanted onto the retina in groups to provide spatial resolution.

13 Claims, 2 Drawing Sheets

TREATING RETINAL DAMAGE BY IMPLANTING THIN FILM OPTICAL DETECTORS

RELATED APPLICATIONS

This application claims priority to U.S. application Ser. No. 60/000,745, filed Jun. 30, 1995.

BACKGROUND OF THE INVENTION

1. Field of Invention

This invention relates to medical implantation for treatment of blindness. More particularly, apparatus and method are provided for treating damaged retina of the eye by implantation of dielectric-based optical micro-detectors onto the retina.

2. Description of Related Art

Damage to the retina of the eye often causes blindness. Such damage can stem from retinal atrophy or Retinitis Pigmentosa (RP). Retinitis Pigmentosa is the most prevalent cause; it is composed of a group of hereditary diseases for which no remedies are currently available. The incidence of such disease is about 0.05 per cent of the total population; however, carriers of RP genes may be as high as 2.5 per cent of the total population. RP is characterized by a progressive loss of rods in both eyes of patients, resulting in sight loss from only night blindness to total blindness. When this loss occurs, retinal neurons remain largely unaffected, according to H. Shichi, *Biochemistry of Vision*, (Academic Press, New York, 1983). Hence, the complex synaptic interconnections at the outer plexiform layer of the eye that would normally transmit photosignals to the nerve ganglions are intact, as are the ganglion axons or bundles which make up the optic nerve.

Previous attempts at remedying retinal blindness problems such as caused by RP have been limited to visual prosthesis which focused on direct stimulation of the brain cortex (G. S. Brinkley and W. S. Lewins, "The Sensations Produced by Electrical Stimulation of the Visual Cortex," *J. of Physiology*, 196, (1968); W. H. Dobelle et al, "Artificial Vision for the Blind: Electrical Stimulation of Visual Cortex Offers Hope for a Functional Prosthesis," *Science* 183, 1974). These attempts involved electrode stimulation of the cortex with resultant patient perception of light. It has also been proposed to replace the damaged eye with an optical "camera" and transmit electrical signals directly to the cortex (W. H. Dobelle, "Artificial Vision for the Blind," *ASAIO Journal*, 1994). These previous attempts have not included implantation of an optical detector onto or into the eye which would send signals through existing nerve cells to the brain.

Since in a case of RP the nerve ganglions are still intact, direct stimulation of the retinal ganglions could be decoded by the brain cortex as light intensity or color. This forms the basis for the concept of implantation of an optical detector onto the retina of a patient with retinal damage such as caused by RP. The local detector can generate a local voltage, thereby electrically exciting the neural circuit. The actual photoexcitation mechanism and resultant "seeing" is a highly complex process, as witnessed by the fact that nearly one-third of all nerve fibers entering the central nervous system are optic nerve fibers. A number of mechanisms have been invoked for optical signal encoding and transmission; however, the process is not well understood except for the agreement that local electric fields can stimulate ganglion electrical activity.

Dielectric detectors that are stable in aqueous solutions and in vivo have been developed recently (H. Lin et al, "Photoresponse and Fast Optical Readout for a $PbZrTiO_3/YBa_2Cu_3O_{7-x}$ Thin Film Capacitor," *App. Phys. Letters*, 66 (1995). Previously developed semiconductor detectors were limited by not being stable in vivo, but the recently-developed detectors are dielectrics (oxides and some nitrides) which are chemically stable in body fluids and which have been shown to exhibit optical detectivity in a thin film capacitor structure. The spectral response is governed by the optical properties of the oxide, and as a result different oxide thin films yield different spectral sensitivity.

There is a need for apparatus and method for providing an electrical field or voltage to stimulate the optical nerve fibers in the eye in response to stimulus by light. The response time of the device should be short enough to make possible effectively an instantaneous response to changes in light stimulation. Multiple sources of electrical voltage should preferably be provided so as to make possible the perception of spatial resolution by the patient. The apparatus should be unaffected by body fluids in the eye and should not be rejected by the body. Preferably, the detector should have means for anchoring on the retina so as not to move after implantation.

SUMMARY OF THE INVENTION

A thin film optical detector based on a dielectric capacitor is provided that can be implanted onto the retina of the eye to generate an electric field when illuminated. The detector will stimulate local nerve endings at the retina in the vicinity of the detector and will produce a signal at the brain (down the optic nerve) that can be perceived by the patient as light. The detectors, having dimensions in the range from about 25 sq microns to about 250,000 sq microns, are implanted onto the retina, preferably in groups, to give spatial resolution to an eye with intact nerves but a damaged retina.

The detectors comprise a dielectric film, preferably with a spectral sensitivity close to that of the human eye. Oxide films with sensitivity that overlaps part of the visible spectrum are useful. Thin film oxides such as $PbZrTiO_3$, $BaSrTiO_3$, $BaVMnO_3$ or nitrides such as BN may be used. The capacitor including the dielectric is preferably formed such that the detector has protuberances on the front side to anchor the detector onto the retina.

DETAILED DESCRIPTION OF THE INVENTION

Figure 1:
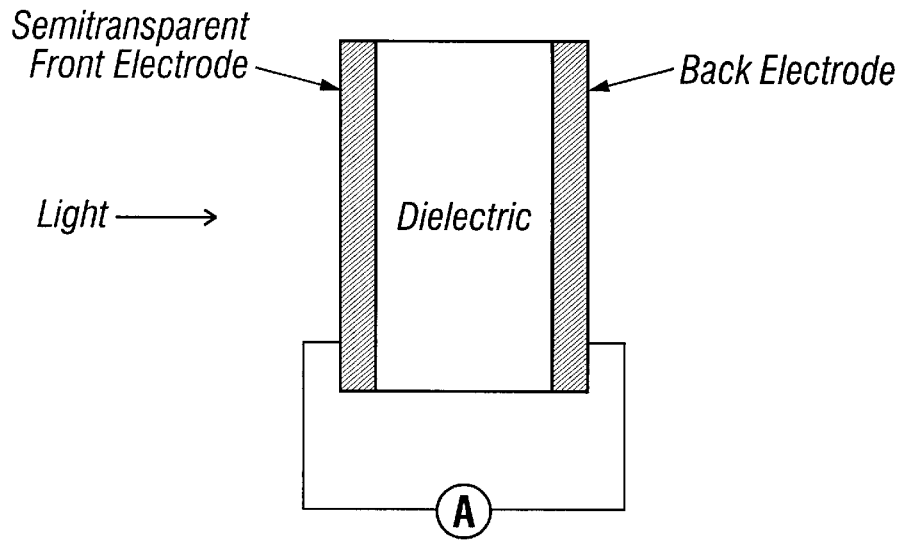
FIG. 1 shows a sketch of a detector of this invention. PRIOR ART

Referring to FIG. 1, a sketch of a thin film capacitor, as described in the paper by Lin et al (referenced above), is shown. The devices are comprised of a dielectric layer with a conducting electrode on either side of the dielectric forming a capacitor-like structure. Illumination of the structure results in a photocurrent generated in the detector with resultant voltage generation when placed into a conducting environment.

For use of such thin film capacitors in the eye, the back electrode (facing the lens of the eye) is made to be semi-transparent and conducting and hence it is made to be thin, preferably having a thickness from about 10 nm to about 50 nm. The front electrode can be thick (greater 500 nm). The total thickness of the detectors can range from less than 1 micron to greater than 100 microns, with the thickness principally determined by the need to handle the detectors for implantation.

The detectors of this invention may be fabricated by pulsed excimer laser deposition (PLD), by sputtering, or by metal organic chemical vapor deposition. The active portion of the detector, the dielectric thin film, is sandwiched between electrically conducting oxide electrodes made from LaSrCoO$_3$ (LSC), YBa$_2$Cu$_3$O$_{7-x}$ (YBCO) or other conducting oxides, or from noble metals (Au, Pt) that are also inert with respect to in vivo environments. LSC is optically transparent and hence is beneficial since it can be used at thicknesses of about 100 nm. A metal electrode may be thinner, with a thickness of about 10 to about 20 nm. These are deposited on an LaAlO$_3$ (LAO) substrate or other substrate that is compatible with high quality dielectric growth, such as SrTiO$_3$ (STO). The dielectric is then grown on the front electrode followed by the back electrode layer. The area and the thickness of the active dielectric layer defines the photocurrent output of the device. These will be dictated by resolution requirements and the level of output required at the retina to excite the nerve cells. A nominal 600 micron diameter oxide detector, having an area of 280,000 sq microns yields photocurrent output of about 2 to 100 picoamps under illumination of about 20 mW/cm$^2$. This level of sensitivity is promising as microvolt level signals are possible in vivo under ambient Air Mass 1 illumination levels of about 100 mW/cm$^2$.

Figure 2:
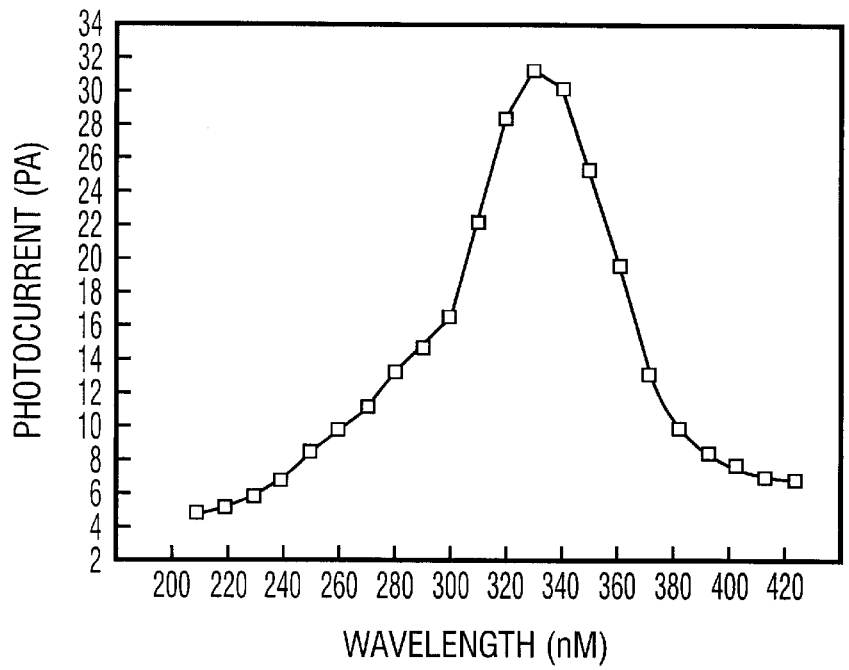
FIG. 2 shows a detector of this invention having stabilization protuberances.

The completed heterostructure stack is patterned to yield single detectors of from 25 sq microns to about 250,000 sq microns in area. This area could be as small as 1 sq micron if implant technologies allow. The substrate (LAO, STO, etc.) may be etched back to expose the transparent or semitransparent front electrode while retaining four corner posts of LAO to act as anchors for the detector on the retina, as shown in FIG. 2. Other designs for anchors can also be applied such as edge bars, cross hatch bars or less/more than four posts to restrain the detector from moving on the outer layer of the retina. Optical radiation striking the font (towards the retina) electrode will then be conveyed to the active dielectric layer resulting in photocurrent generated across the two electrodes of the detector. This photocurrent will result in a local voltage which will stimulate the retinal nerve endings localized near the detector.

A variety of dielectrics can be used in the detectors. In fact, dielectric films that are sensitive in the ultraviolet (for example) could be implanted to enhance visibility (or at least sensitivity to light) in that wavelength range, i.e. the response of a human eye to light can be shifted toward the ultraviolet or the infrared (but with limited resolution) by such an implant.

Oxides and many nitrides are generally highly chemically stable materials, and hence are quite immune to the rather harsh aqueous in vivo environment of the eye. This factor allows for the implant of oxide/nitride detectors directly into the eye. This is not a possibility with semiconductor (usually p-n junction) detectors because of their chemical instability. Those types of detectors would require encapsulation and wiring to attempt to make them work, according to J. Wyatt et al, "Development of a Silicon Retinal Implant," *Proc. of Investigative Ophthalmology & Visual Sci. Conf.,* Sponsored by Assoc. for Res. in Vision & Opth., May, 1995). Because of the inertness of the oxides and nitrides of this invention, the dielectric detectors can be directly implanted onto the retina with limited or no degradation of detector characteristics. In addition, the human body is not significantly adversely affected by most oxide materials, There is as a result, an expectation of minimal, if any, infection due to, or rejection of these dielectric detectors. The detectors would use either conductive oxide electrodes or noble metal electrodes of gold or platinum, both of which are quite benign to the human body.

The time response of the detectors of this invention is more than rapid enough for full-motion video. The rise time of electrical output signal with an optical input was measured to be less than 30 ns and the signal decay time was of the order of 1 microsecond. This means that in their use for human detection of light, there will be no time delay in identification of features by the brain.

Figure 3:
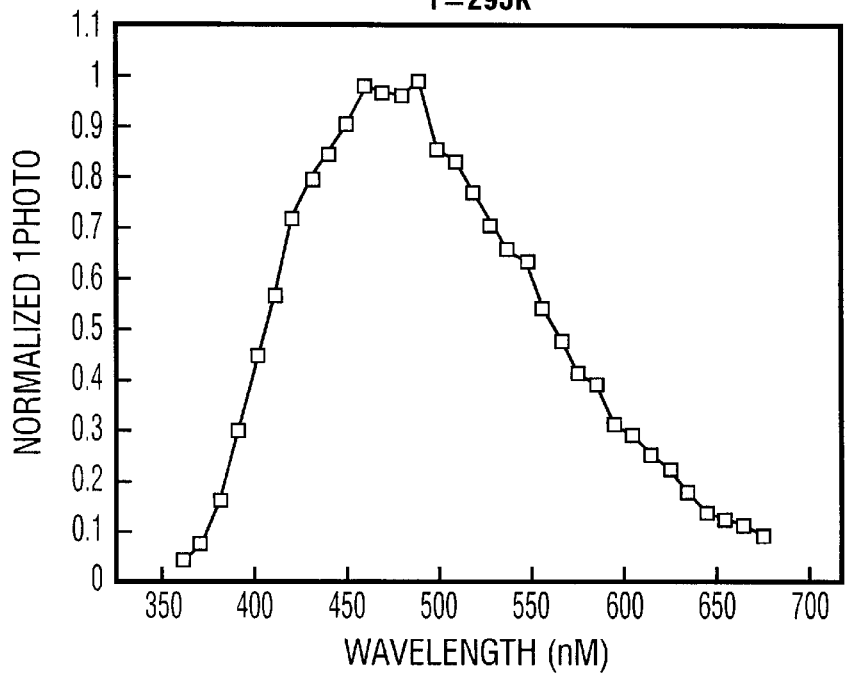
FIG. 3 shows a graph of the photoresponse of another of the detectors of this invention.

The photoresponse of a detector of this invention having a Au/BST/YBCO structure is shown in FIG. 3. Photocurrent in picoamperes is plotted vs. wavelength of incident light in nm, as measured at a temperature of 300° K. The optical sensitivity is primarily in the blue but overlaps partially the spectral sensitivity of the human eye.

Figure 4:
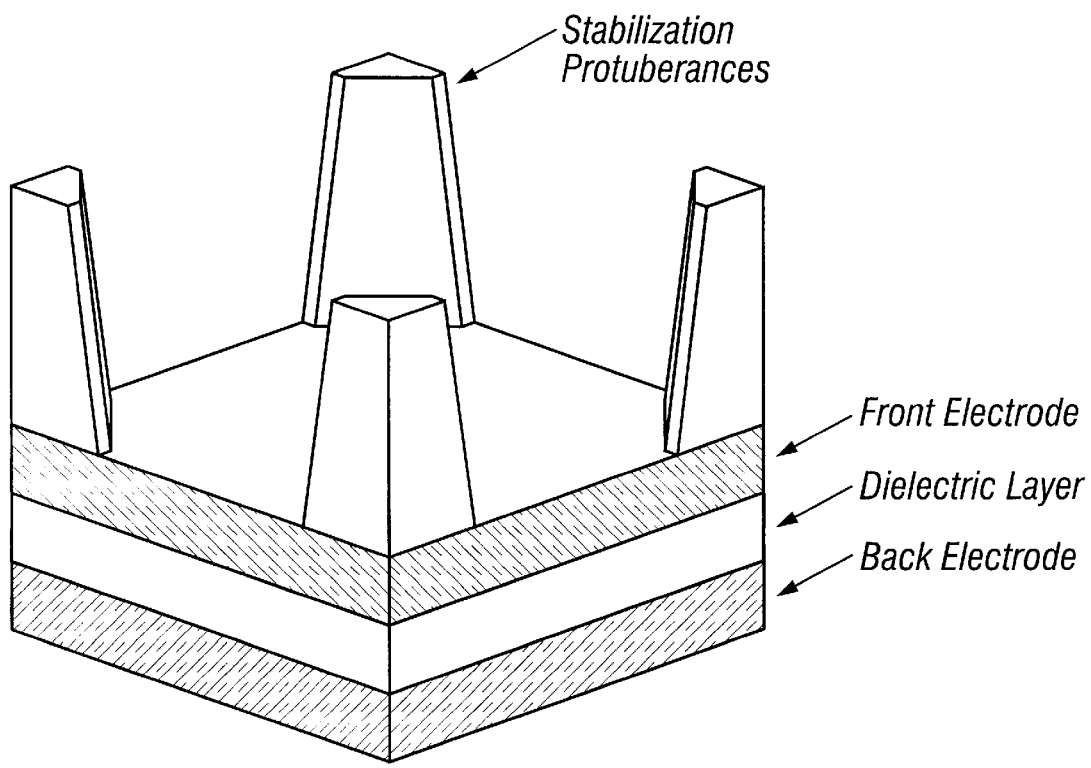
FIG. 4 shows a graph of the photoresponse of one of the detectors of this invention.

The photoresponse of another detector of this invention, a Au/BVM/YBCO structure, is shown in FIG. 4. Its spectral response overlaps almost all of the spectral sensitivity range of the human eye. Comparison of FIG. 3 and FIG. 4 shows the peak in response is in the blue region for BaSrTiO$_3$ (FIG. 3) and in the red region for BaVMnO$_3$ (FIG. 4).

The detectors may be attached to the plexiform layer of the retina singly or in several discrete positions, e.g. four diametrically opposed positions, so that their localized voltage outputs could be used to distinguish up/down/left/right. When irradiated with light through the lens of the eye, an electric field is generated across the detector that stimulates the ganglia of the retina, resulting in a signal down the optic nerve that may be translated by the cortex of the brain as "seeing light". The distribution of the detectors on the retina gives spatial sensitivity to "seen" light since different sections of the retina (the points at which the detectors are implanted) would see different local electric fields from specific detectors. The detectors, therefore, utilize the neural logic and operating system already existing in the eye/brain. They can therefore, be used under patient conditions that show intact optic nerve and retinal ganglia (nerve endings), but damaged retinal detectors such as in Retinitis Pigmentosa.

The thin film dielectric detector scheme has the ability to increase the extent of the detector system to cover significant portions of the retina through reduction of the size of the detectors and increase in their number with a resultant increase in resolution.

Although implantation in the human eye is the primary application of this invention, implantation in the eye of any animal having damaged retina and intact optical nerves can provide additional sensitivity to light for that animal.

Having described the invention above, various modifications of the techniques, procedures, methods, materials and equipment will be apparent to those in the art. It is intended that all such variations within the scope and spirit of the appended claims be embraced thereby.

What is claimed is:

1. A method for providing electrical signals to replace signals from damaged retinal photoreceptors of a retina in an eye, comprising the steps of:

providing a dielectric capacitor-type photodetector, the photodetector comprising a front and a back electrode and a dielectric thin film sandwiched between the electrodes; and implanting the photodetector onto the retina of the eye so as to produce electrical signals from the photodetector.

2. The method of claim 1 wherein at least one of the electrodes is made from a conducting oxide material.

3. The method of claim 2 wherein the oxide material is selected from the group of oxides consisting of $LaSrCoO_3$ (LSC) and $YBa_2Cu_3O_{7-x}$ (YBCO).

4. The method of claim 1 wherein at least one of the electrodes is made of a noble metal.

5. The method of claim 1 wherein the dielectric thin film is comprised of an oxide or nitride.

6. The method of claim 5 wherein the oxide or nitride is selected from the group of oxides and nitrides consisting of $PbZrTiO_3$, $BaSrTiO_3$, $BaVMnO_3$, and BN.

7. The method of claim 5 wherein the dielectric film is selected to enhance visibility in a selected wave length range of light.

8. The method of claim 7 wherein the dielectric film is sensitive in the ultraviolet wavelength range.

9. The method of claim 7 wherein the dielectric film is sensitive in the infrared wavelength range.

10. The method of claim 1 wherein the front electrode includes means for anchoring the photodetector on the retina of the eye.

11. The method of claim 1 further comprising the step of implanting a plurality of photodetectors onto the retina of the eye.

12. The method of claim 11 wherein the photodetectors are implanted at locations such as to provide spatial sensitivity to the detected light.

13. The method of claim 1 wherein the photodetector has an area from about 1 sq micron to about 250,000 sq microns.

* * * * *